United States Patent [19]

Günther

[11] 4,452,743

[45] * Jun. 5, 1984

[54] PROCESS FOR THE SEPARATION OF OILS AND/OR PHOSPHATIDYLETHANOLAMINE FROM ALCOHOL SOLUBLE PHOSPHATIDYLCHOLINE PRODUCTS CONTAINING THE SAME

[75] Inventor: Bernd-Rainer Günther, Bergheim-Fliesteden, Fed. Rep. of Germany

[73] Assignee: A. Nattermann & Cie GmbH, Cologne, Fed. Rep. of Germany

[*] Notice: The portion of the term of this patent subsequent to Apr. 17, 2001 has been disclaimed.

[21] Appl. No.: 326,322

[22] Filed: Dec. 1, 1981

[30] Foreign Application Priority Data

Dec. 13, 1980 [DE] Fed. Rep. of Germany ....... 3047011

[51] Int. Cl.$^3$ ............................ A23J 7/00; C07F 9/02; C11C 3/00
[52] U.S. Cl. .................................................... 260/403
[58] Field of Search ........................................ 260/403

[56] References Cited

U.S. PATENT DOCUMENTS

| | | | |
|---|---|---|---|
| 2,724,649 | 11/1955 | Julian | 99/123 |
| 2,727,046 | 12/1955 | Scholfield et al. | 260/403 |
| 3,031,478 | 4/1962 | Klenk et al. | 260/403 |
| 3,268,335 | 8/1966 | Circle et al. | 99/15 |
| 3,436,413 | 4/1969 | Okany | 260/403 |
| 3,661,946 | 5/1972 | Pardun | 260/403 |
| 3,694,473 | 9/1972 | Eibl et al. | 260/403 |
| 3,704,254 | 11/1972 | Aneja | 260/403 |
| 3,752,833 | 8/1973 | Aneja | 260/403 |
| 3,798,246 | 3/1974 | Shimazaki et al. | 260/403 |
| 3,869,482 | 3/1975 | Wolfe | 260/403 |
| 4,235,793 | 11/1980 | Betzing | 260/403 |
| 4,323,563 | 4/1982 | Takami et al. | 260/403 X |

FOREIGN PATENT DOCUMENTS 1113241 5/1968 United Kingdom .

*Primary Examiner*—Helen M. S. Sneed
*Attorney, Agent, or Firm*—Pearne, Gordon, Sessions, McCoy, Granger & Tilberry

[57] ABSTRACT

The present invention is related to a new process for the separation of oil and/or phosphatidylethanolamine from alcohol soluble phosphatidylcholine products containing the same thus producing, by chromatography on silicic acid gel in a lower alkanol containing 1 to 4 carbon atoms as solvent and/or eluant, a phosphatidylcholine product containing oils and/or phosphatidylethanolamine in a definite diminished amount.

3 Claims, No Drawings

PROCESS FOR THE SEPARATION OF OILS AND/OR PHOSPHATIDYLETHANOLAMINE FROM ALCOHOL SOLUBLE PHOSPHATIDYLCHOLINE PRODUCTS CONTAINING THE SAME

The present invention is related to a new process for the separation of oils and/or phosphatidylethanolamine from alcohol soluble phosphatidylcholine products containing the same, thus producing, by chromatographic adsorption on silicic acid gel, a phosphatidylcholine product containing oils and/or phosphatidylethanolamine in a definite diminished amount.

In the food industry and in cosmetics industry, phosphatide products are desired which besides phosphatidylcholine contain oils and/or phosphatidylethanolamine in definite diminished amounts which are diminished over the content in phosphatidylcholine products obtainable from naturally occurring phospholipid.

The crude phosphatides from plant origin recovered in the production of edible oil besides phosphatidylcholine contain phosphatidylethanolamine and mono-, di- and triglycerides (hereinafter referred to as oils) as well as phosphatidylinosite and other phosphorus containing glycerol esters and products such as peptides, amino acids, sterines, sterineester, free fatty acids and hydrocarbon derivatives. In general the crude phosphatide from plant origin is deoiled in a first step with acetone (U.S. Pat. No. 3,268,335) and then in a second step is extracted with ethanol (U.S. Pat. No. 2,724,649). In a third step, the phosphatide fraction soluble in ethanol is subjected to adsorption chromatography at temperatures not exceeding 35° C. (U.S. Pat. No. 3,031,478). During oil separation by means of acetone, small amounts of acetone derivatives such as mesityloxide, diacetone alcohol, phorone and others are formed. The separation of these by-products which are toxic and particularly disturbing by their characteristic smell is either most burdensome or even impossible. Furthermore, during removal of oil by means of acetone, increase of peroxide formation occurs which compounds have known undesirable physiological properties.

The alcoholic extraction of crude phosphatides of plant origin yields in an oil-containing phosphatide fraction U.S. Pat. No. 4,235,793, British Pat. No. 1,113,241, and U.S. Pat. No. 3,661,946 allowing recovery of an oil-containing phosphatidylcholine free of phosphatidylethanolamine by chromatographic purification at room temperature. An own invention U.S. patent application Ser. No. 06/269,805 allows to separate the oil by the addition of small amounts of water and to obtain a highly purified oil-free phosphatidylcholine. However, this aqueous oil removal which is suitable for the production of certain phosphatide fractions, represents a three step process (extraction, chromatography, oil-removal) in the production of an oil-free phosphatidylcholine. A further disadvantage is the removal of water from the ethanol solvent.

All these processes are directed to the separation of the total amount of side products of phosphatidylcholine. No process may be controlled such that phosphatidylcholine products are produced having a very definite preselected content in oil and/or phosphatidylethanolamine. It is a further disadvantage of the known processes on a technical scale that the adsorbent used, i.e., the basic aluminum oxide, is loaded with the impurities, in particular with phosphatidylethanolamine and therefor has to be discarded. A further disadvantage is the formation of lysophosphatidylcholine during chromatography (O. Rengkonen, J. Lipid. Res. vol. 3, pgs. 181 to 183 (1962), D. Van Damme et al., Int. Symp. Chromatogr. Elektrophoresis, 5th vol. 1968 (published 1969), pgs. 268 to 278).

Chromatography on silicic acid gel up to now only has been used analytically or on a laboratory scale. Thus, phosphatides in hexane solution are not adsorbed on silicic acid gel (Japanese patent application No. 77012202, U.S. Pat. No. 3,869,482), while they are kept back in alcoholic solution on silicic acid gel (H. Richter et al., Pharmazie, 1977, vol. 32 (3), p. 164). This difference in property is explained with the formation of lipophilic, polymolecular phosphatide micells in hexane over the phosphatides present as single molecule in alcohol. Chromatography again is carried out at room temperature. The separation and selective desorption of the phosphatides occurs either with alcohol/ammonia (Japanese patent specification No. 49093400) or with mixtures of chloroform and methanol (C. H. Lea et al., Biochem. J., vol. 60 (1965), pgs. 353 to 363) or with chloroform/methanol/water (East German Pat. No. 79 916) when using alcoholic phosphatide solutions. However, it was not possible to transfer these procedures to a technical scale since always toxic components have been used in the eluant mixtures such as ammonia or chloroform and the recovery and removal thereof was very burdensome from the final lecithine.

Phosphatidylcholine crude products as they are in trade, in particular from soybeans represent products which have been obtained by extraction with alcohol and which are soluble in alcohol and contain as main by-product oil and phosphatidylethanolamine. However, there are also phosphatidylethanolamine crude products which as described contain only one or the other of the two main by-products. It is an object of the present invention to provide a technical process for the separation of oils and/or phosphatidylethanolamine from alcohol soluble phosphatidylcholine crude products containing the same producing such phosphatidylcholine products having the one or both of these by-products in a definite, over the trade products diminished amount thereof, depending upon the requests for their use in the food industry or in cosmetic industry.

It has been surprisingly found that when starting from alcohol soluble phosphatide fractions containing oils and/or phosphatidylethanolamine and subjecting them to a column chromatography using silicic acid gel at an elevated temperature such phosphatidylcholine products may be obtained.

The process according to the present invention for separating oil and/or phosphatidylethanolamine from alcohol soluble phosphatidylcholine products containing the same with the production of phosphatidylcholine products containing oils and phosphatidylethanolamine in definite diminished amounts is characterized in that a solution of the alcohol soluble phosphatidylcholine product containing oils and/or phosphatidylethanolamine, in a lower alkanol having from 1 to 4 carbon atoms or a mixture of several of such alkanols, said alkanol or mixture of several alkanols possibly containing up to 20% by volume of water, is put on a column of silicic acid gel at an elevated temperature below 60° C., the column at this temperature with a lower alkanol having from 1 to 4 carbon atoms or a mixture of several such alkanols, said alkanol or mixture of alcohols possibly containing up to 20% by volume of water, and at first separating a preeluate containing oils and/or phosphatidylethanolamine in amounts sufficient to lower the content of such products in the phosphatidylcholine as desired and collecting thereafter separately a main eluate and separating the solvent therefrom in usual manners. Preferably the used solvent is applied also as eluant making the present process particularly simple. The preferred lower alkanol having from 1 to 4 carbon atoms is ethanol.

The amount of preeluate depends upon the phosphatidylcholine starting product and the amount of oils and/or phosphatidylethanolamine desired to be separated. Depending upon the used phosphatidylcholine starting product, the preeluate contains also the other usually present by-products such as sterines, sterine derivatives, glycolipids and phospholipids. They can be further used in known manners.

By simple analytic methods it can be determined from when at each selected elevated temperature the preeluate contains the amount of oils and/or phosphatidylethanolamine which is to be separated over the phosphatidylcholine starting product, thus allowing to collect a main eluate which after separation of the solvent yields in a phosphatidylcholine product which contains oils and/or phosphatidylethanolamine in a definite diminished amount over the starting product as desired.

The silicic acid gels are known products usual in chromatography having varying grain size. They furthermore can be pressed silicic acid gel. Such silicic acid gel products may be activated or deactivated; and Most preferred are neutral silicic acid gel products.

The process according to the present invention may be carried out at normal pressure or at higher pressures. It is a particular advantage of the process of the present invention that the silicic acid gel may repeatedly be used. After collection of the main eluate there is only adsorbed a small amount of phosphatidylcholine. A further advantage of silicic acid gel used in the present process are the high amounts which can be adsorbed. Thus, by carrying out the present process with 100 parts by weight of silicic acid gel about 60 parts by weight of solid material may be separated from the alcohol soluble phosphatide fraction.

EXAMPLES

Analysis

The phosphatides are analysed by thin layer chromatography. The oil content is equal the products which may be dialysed. The water content is determined according to Karl Fischer and the ethanol content is determined by gas chromatography.

Column chromatography

There is used a usual heatable column (inner diameter 4.5 cm., length 37 cm.). The column is combined with a heat exchanger in order to guarantee equal column temperature and starting temperature. The column is prepared from a slurry of 200 g. of silicic acid gel (Merck, Darmstadt/Germany) in the applied solvent. The silicic acid gel may be reused after used in the present process.

Starting materials

Crude soybean phosphatide is extracted at 35° C. with 95% ethanol using 1 part by weight of crude phosphatide for 2.5 parts by weight of ethanol. The sedimented solid material is separated at room temperature from the supernatant ethanol phase. The ethanol phase is evaporated. The resulting solid material showed the following analysis:
Phosphatidylcholine (PC): 43%
Phosphatidylethanolamine (PE): 12%
Oils: 21%
This solid material was used in Example 1.

The solid material used in Example 2 has been prepared as follows:
Soybeanphosphatide is deoiled with acetone and thereafter is extracted with 95% ethanol. The ethanol soluble phosphatide fraction is evaporated and analysed with the following result:
PC content: 52%
PE content: 20%
An oil containing phosphatidylcholine product free of phosphatidylethanolamine is prepared as described in U.S. Pat. No. 4,235,793 (Example 3).

Example 1

118 g. of solid materials are dissolved in 275 g. of 95% ethanol. This solvent is used also as eluant for producing a total of 4 l. of eluate. The applied temperatures of the column and solution were as follows: 30° C., 40° C., 50° C., 55° C.

1 l. of preeluate is collected, whereafter a total of 3 l. of main eluate is collected. The main eluate is evaporated and analysed as follows from the following table:

| Temperature of column | Yield in[1] solids | Composition | | | |
|---|---|---|---|---|---|
| | | PC | PE | Oil | Others[2] |
| 30° C. | 53% | 53% | 17% | 25% | 5% |
| 40° C. | 42% | 67% | 11% | 17% | 5% |
| 50° C. | 37% | 77% | 7% | 11% | 5% |
| 55° C. | 35% | 86% | 3% | 6% | 5% |

[1]calculated to the starting solid material in % of the theoretical.
[2]other components

Example 2

110 g. of solid materials are dissolved in 40 g. of 95% ethanol, the solution is put to the column. 95% ethanol is used also as eluant. A total of 4 l. of eluate is collected. Adsorption and elution occurs at 50° C.

There are at first collected 1 l. of preeluate, thereafter 3 l. of main eluate. The main eluate is evaporated and analysed.
Yield in solid material: 30% of the theoretical
PC content: 86%
PE content: 8%
Oil content: <1%
PC yield calculated to the starting solid material: 50% of the theoretical

Example 3

There are put to the column 80 g. of solid material dissolved in 30 g. of 95% ethanol. The solvent was also used as eluant to produce a total of 4 l. of eluate. The temperature of the column was 40° C.

After collecting 0.3 l. of preeluate there are collected a total of 3.7 l. of main eluate. The main eluate is evaporated and analysed:
Yield in solid material: 68% of the theoretical
PC content: 80%
Oil content: 15%
PC yield calculated to the starting solid material: 80% of the theoretical

What I claim is:

1. Process for the separation of oils and/or phosphatidylethanolamine from phosphatidylcholine products containing the same with the production of phosphaditylcholine products containing oils and phosphatidylethanolamine in definite diminished amounts, characterized in that the solution of an alcohol soluble phosphatidycholine product containing oils and/or phosphatidylethanolamine in a lower alkanol containing from 1 to 4 carbon atoms or in a mixture of several such alcohols, said alkanol or mixtures containing up to 20% by weight of water, at an elevated temperature below 60° C. are put on to a silicic acid gel column, the column is eluated at this temperature with a lower alkanol having from 1 to 4 carbon atoms or a mixture of such alkanols, said alkanol or mixture containing up to 20% by weight of water, a preeluate is collected containing oils and/or phosphatidylethanolamine in such an amount as the content in the phosphatidylcholine product is desired to be diminished and, separate therefrom, a main eluate is collected and the solvent is separated from said main eluate.

2. Process according to claim 1 characterized in that the same solvent is used for dissolving the phosphatidylcholine starting product and for eluating the silicic acid gel column.

3. Process according to claims 1 or 2 characterized in that the lower alkanol having from 1 to 4 carbon atoms is ethanol.

* * * * *